United States Patent
Iwamoto

(10) Patent No.: US 8,611,494 B2
(45) Date of Patent: Dec. 17, 2013

(54) METHOD FOR DISASSEMBLING LIQUID CRYSTAL DISPLAY DEVICE

(71) Applicant: Panasonic Corporation, Osaka (JP)

(72) Inventor: Hiroshi Iwamoto, Osaka (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 13/790,877

(22) Filed: Mar. 8, 2013

(65) Prior Publication Data
US 2013/0195242 A1    Aug. 1, 2013

Related U.S. Application Data

(63) Continuation of application No. PCT/JP2012/002674, filed on Apr. 18, 2012.

(30) Foreign Application Priority Data

Oct. 21, 2011   (JP) .................. 2011-231386

(51) Int. Cl.
  *G01N 23/223* (2006.01)
  *G01N 23/04* (2006.01)
  *G01N 23/06* (2006.01)

(52) U.S. Cl.
  USPC ............. 378/46; 378/45; 378/53; 378/88; 378/90

(58) Field of Classification Search
  USPC .................. 378/45, 46, 53, 57, 88, 90
  See application file for complete search history.

(56) References Cited

U.S. PATENT DOCUMENTS 7,416,462 B2 *   8/2008   Noma et al. ............... 445/2
2013/0195242 A1*  8/2013   Iwamoto ............... 378/45

FOREIGN PATENT DOCUMENTS

| JP | 09-057698 | 4/1997 |
| JP | 2001-305501 | 10/2001 |
| JP | 2001-337305 | 12/2001 |
| JP | 2008-090225 | 4/2008 |
| JP | 2009-056437 | 3/2009 |

OTHER PUBLICATIONS

International Search Report dated Jul. 17, 2012 from corresponding PCT Application No. PCT/JP2012/002674.

* cited by examiner

*Primary Examiner* — Thomas R Artman
(74) *Attorney, Agent, or Firm* — McDermott Will & Emery LLP

(57) ABSTRACT

In the present disclosure, before disassembly of liquid crystal module (1) having liquid crystal panel (2) and a back light, irradiation is performed with X-rays (13) from the front surface side of liquid crystal panel (2) of liquid crystal module (1). By this irradiation with X-rays (13), generated fluorescent X-rays (14) are detected to analyze an element contained in liquid crystal panel (2), while X-rays (17) backscattered or transmitted to the rear surface side of liquid crystal module (1) are detected to determine a type and a state of the back light. Then, based on the determined type and state of the back light, liquid crystal module (1) is disassembled.

1 Claim, 2 Drawing Sheets

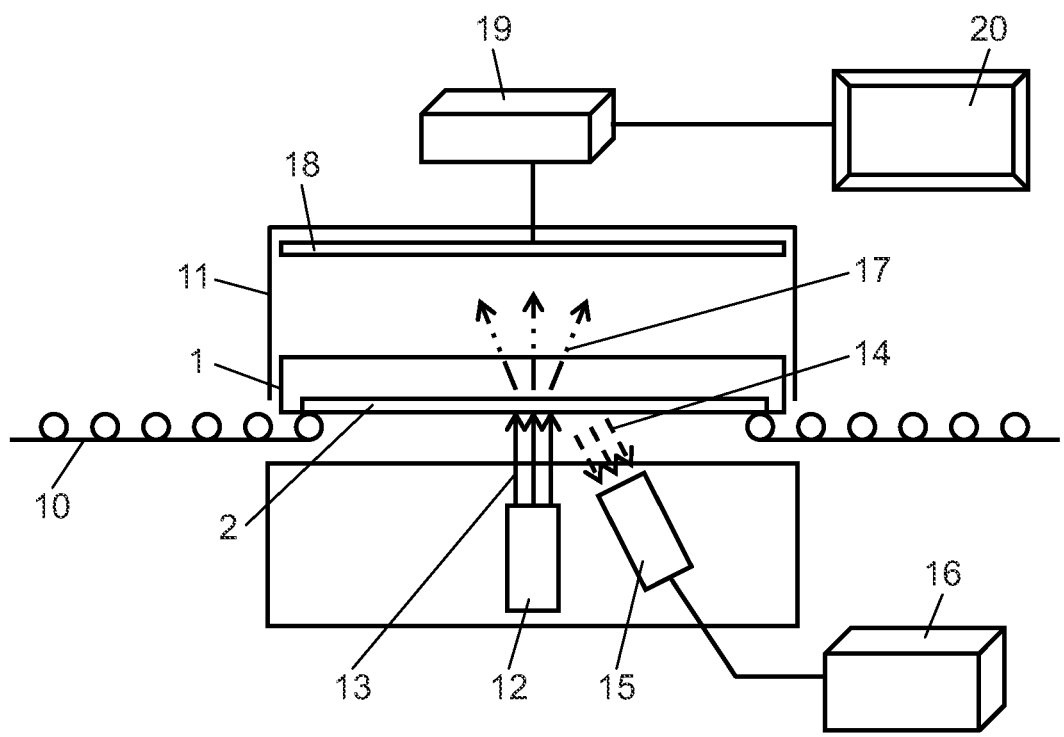

METHOD FOR DISASSEMBLING LIQUID CRYSTAL DISPLAY DEVICE

RELATED APPLICATIONS

This application is a continuation of International Application No. PCT/JP2012/002674, filed on Apr. 18, 2012, which in turn claims the benefit of Japanese Application No. 2011-231386, filed on Oct. 21, 2011, the disclosures of which Applications are incorporated by reference herein.

TECHNICAL FIELD

The present disclosure relates to a method for disassembling a liquid crystal display device.

BACKGROUND ART

In recent years, as display devices appropriate for slimming and upsizing, flat-panel televisions, such as liquid crystal televisions using liquid crystal display panels and plasma televisions using plasma display panels, have been mass-produced and sales thereof have been expanded. Therewith, the number of waste of used flat-panel televisions is on the gradual increase. From viewpoints of environmental issues and resource savings, it is becoming important to improve a system for disassembling a variety of members and materials of a used flat-panel television into a recyclable form, and an efficient disassembly processing method has been required.

For example, recycling of a variety of members and materials used for a liquid crystal display device requires disassembly and classification with respect to each type of the materials. Further, a material containing a substance of concern or the like needs to be subjected to appropriate processing.

As a method for disassembling a liquid crystal display device, for example, a method disclosed in PTL 1 is hitherto known. This PTL 1 discloses a method for disassembling a waste liquid crystal display device provided with a back light. Specifically, the method for disassembling a waste liquid crystal display device is disclosed which includes the steps of: removing a cabinet from a waste liquid crystal display device; removing a control substrate from the waste liquid crystal display device, from which the cabinet has been removed; and removing a back light.

Since mercury is sealed in a fluorescent tube used for the back light of the liquid crystal display device and the fluorescent tube itself has a structure easily prone to damage, the fluorescent tube may be damaged during a disassembly operation, or may be damaged while being collected or carried. When it is damaged, there is a risk that an operator performing disassembly might breathe in mercury.

CITATION LIST

Patent Literature

PTL 1: Unexamined Japanese Patent Publication No. 2008-90225

SUMMARY

In the present disclosure, before disassembly of a liquid crystal module having a liquid crystal panel and a back light, irradiation is performed with X-rays from the front surface side of the liquid crystal panel of the liquid crystal module. By this irradiation with X-rays, generated fluorescent X-rays are detected to analyze an element contained in the liquid crystal panel, while X-rays backscattered or transmitted to the rear surface side of the liquid crystal module are detected to determine a type and a state of the back light. Then, based on the determined type and state of the back light, a method for disassembling the liquid crystal module is decided.

BRIEF DESCRIPTION OF DRAWINGS

FIG. 2 is an explanatory view of an inspection device for explaining a method for disassembling the liquid crystal display device in the embodiment of the present disclosure.

DESCRIPTION OF EMBODIMENT

Figure 1:
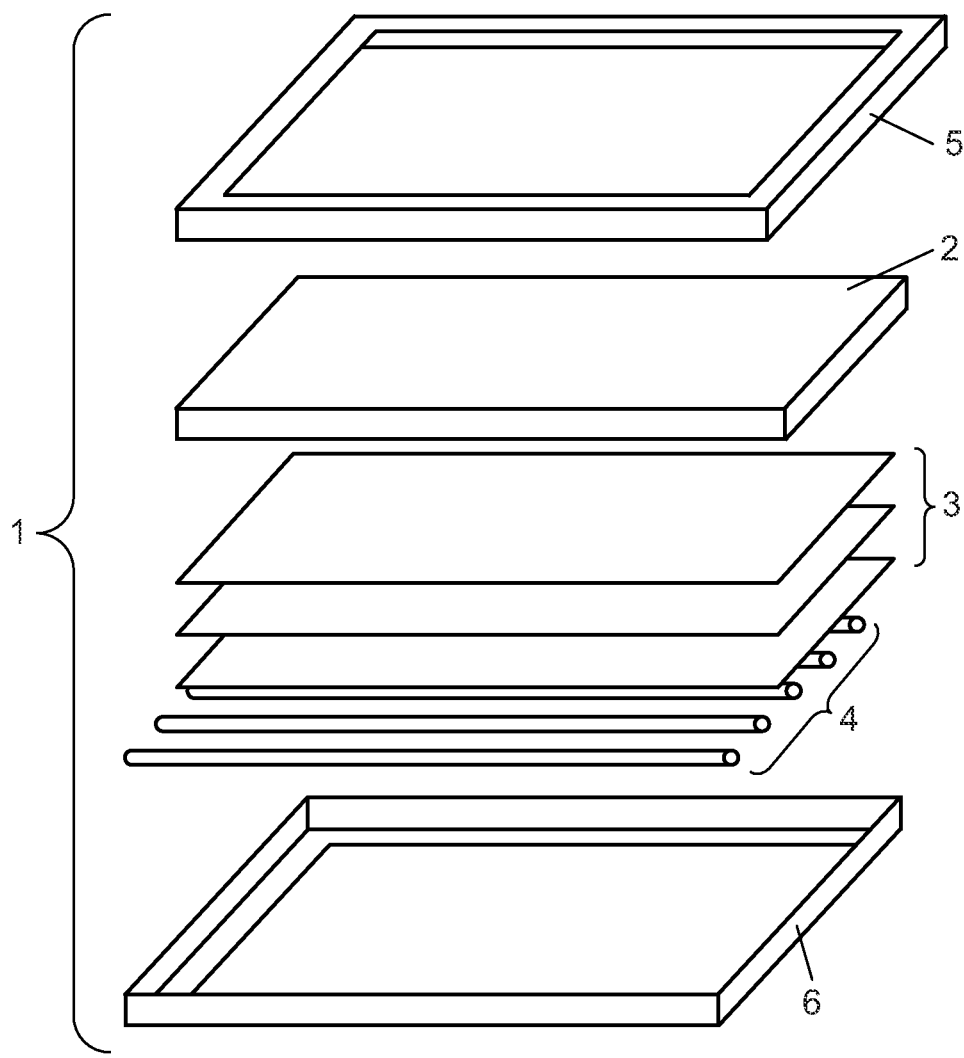
FIG. 1 is an exploded perspective view of a liquid crystal module of a liquid crystal display device in an embodiment of the present disclosure.

Hereinafter, a method for disassembling a liquid crystal display device in an embodiment of the present disclosure will be described with reference to the drawings.

FIG. 1 is an exploded perspective view showing a configuration of a liquid crystal module of the liquid crystal display device in the embodiment of the present disclosure. As shown in FIG. 1, liquid crystal module 1 is configured in combination of liquid crystal panel 2, optical sheet 3, back light 4, and front outer frame 5 and rear outer frame 6 for housing them. Further, front outer frame 5 is fastened with rear outer frame 6 by screws or the like. Back light 4 is configured of a plurality of fluorescent tubes, and above this back light 4, optical sheet 3 and liquid crystal panel 2 are respectively arranged in this order.

Next, in terms of such a liquid crystal display device, there will be described a method for disassembling a used liquid crystal display device at the end of its product life.

FIG. 2 is an explanatory view showing an inspection device of liquid crystal module 1 in the disassembly method in the embodiment of the present disclosure.

First, liquid crystal module 1 is taken out of the liquid crystal display device, and placed on carrier device 10 with the liquid crystal panel 2 side turned downward. By the drive of this carrier device 10, liquid crystal module 1 is moved to an inspection section as shown in FIG. 2. At this time, X-ray shielding housing 11 descends from above for preventing leakage of X-rays.

Next, in the inspection section, irradiation is performed with X-rays 13 from X-ray source 12 located below liquid crystal module 1 toward liquid crystal panel 2. The irradiation with X-rays 13 leads to generation of fluorescent X-rays 14, and fluorescent X-rays 14 are detected by X-ray detector 15. Then, based on fluorescent X-rays 14 detected by X-ray detector 15, an element in glass of liquid crystal panel 2 is analyzed by analyzer 16. In this analysis, presence or absence of a substance of concern such as arsenic or antimony is judged while an element of a glass component and its proportion are analyzed. Then, based on this analysis, a type of glass is identified.

Further, the irradiation of liquid crystal panel 2 with X-rays 13 leads to scattering or transmission of X-rays 13 also to the rear surface side of liquid crystal module 1. These backscattered or transmitted X-rays 17 are detected by detection sensor 18. Based on X-rays 17 detected by this detection sensor 18, an image is processed by image processing device 19 and observed by monitor 20, to judge a type (fluorescent tube, LED or the like) of back light 4, and judge cracking in the fluorescent tube as back light 4.

Based on the inspection results as thus described, the materials used for liquid crystal module 1 and the type and the state, such as cracking, of back light 4 are grasped, and based on the grasped results, a subsequent disassembly process is decided. Specifically, when the fluorescent tube used for back light 4 is damaged, in order to prevent the operator from breathing in mercury during disassembly, appropriate action is taken, such as performing an operation wearing protective equipment. Further, classification is performed in accordance with a type of the glass material of liquid crystal panel 2.

As thus described, according to the embodiment of the present disclosure, before disassembly of the liquid crystal module, irradiation is performed with X-rays from the front surface side of the liquid crystal panel, and by generated fluorescent X-rays, an element contained in panel glass is analyzed. Then, presence or absence of a substance of concern is decided and a component element of panel glass and its proportion are analyzed, to identify a type of the glass, thereby allowing appropriate processing in the post-process, so as to seek a more efficient disassembly operation. Further, based on the backscattered or transmitted X-rays, the state of the back light is observed by means of an image, to judge a structure and a type of the back light and the presence or absence of cracking in the fluorescent tube used for the back light, thereby allowing selection of appropriate processing in the post-process, so as to ensure safety of the disassembly operation.

INDUSTRIAL APPLICABILITY

The present disclosure makes it possible to process a liquid crystal display device in an efficient and appropriate manner while ensuring safety of a processing operation, and is useful in recycling the liquid crystal display device.

REFERENCE MARKS IN THE DRAWINGS 1 liquid crystal module
2 liquid crystal panel
3 optical sheet
4 back light
5 front outer frame
6 rear outer frame
10 carrier device
11 X-ray shielding housing
12 X-ray source
13, 17 X-rays
14 fluorescent X-rays
15 X-ray detector
16 analyzer
18 detection sensor
19 image processing device
20 monitor

The invention claimed is:

1. A method for disassembling a liquid crystal display device,
the method comprising:
before disassembly of a liquid crystal module having a liquid crystal panel and a back light, irradiating the module with X-rays from a front surface side of the liquid crystal panel of the liquid crystal module to detect generated fluorescent X-rays for analyzing an element contained in the liquid crystal panel, as well as to detect X-rays backscattered or transmitted to a rear surface side of the liquid crystal module for determining a type and a state of the back light; and
thereafter, based on results of the analysis of the element and the detection of the X-rays, deciding a method for disassembling the liquid crystal module.

* * * * *